United States Patent
Paydar

(10) Patent No.: US 11,213,425 B2
(45) Date of Patent: Jan. 4, 2022

(54) VITRECTOMY INSTRUMENT WITH MULTIPLE ROTATING CUTTING EDGES

(71) Applicant: Alcon Inc., Fribourg (CH)

(72) Inventor: Omeed Paydar, Irvine, CA (US)

(73) Assignee: Alcon Inc., Fribourg (CH)

( * ) Notice: Subject to any disclaimer, the term of this patent is extended or adjusted under 35 U.S.C. 154(b) by 350 days.

(21) Appl. No.: 16/374,206

(22) Filed: Apr. 3, 2019

(65) Prior Publication Data

US 2019/0314201 A1    Oct. 17, 2019

Related U.S. Application Data

(60) Provisional application No. 62/656,230, filed on Apr. 11, 2018.

(51) Int. Cl.

| *A61F 9/007* | (2006.01) |
| *A61B 17/32* | (2006.01) |
| *A61B 17/00* | (2006.01) |
| *A61M 1/00* | (2006.01) |

(52) U.S. Cl.
CPC .... *A61F 9/00763* (2013.01); *A61B 17/32002* (2013.01); *A61B 2017/00544* (2013.01); *A61M 1/774* (2021.05)

(58) Field of Classification Search
CPC .. A61F 9/007; A61F 9/00736; A61F 9/00763; A61B 17/32; A61B 17/32002; A61B 17/320016; A61B 17/3207; A61B 2017/00544; A61B 2017/320024; A61B 2017/320028; A61B 2017/320032; A61B 2017/32004; A61M 1/774
See application file for complete search history.

(56) References Cited

U.S. PATENT DOCUMENTS

| 4,577,629 | A | * | 3/1986 | Martinez | ............. A61F 9/00763 |
| | | | | | 604/22 |
| 5,019,035 | A | | 5/1991 | Missirlian | |
| 5,176,628 | A | | 1/1993 | Charles | |
| 5,474,532 | A | | 12/1995 | Steppe | |

(Continued)

OTHER PUBLICATIONS

Charles, S., Fluidics and Cutter Dynamics, Physics matter in deciding on cut rates and duty cycles, Retinal Physician, Apr. 1, 2012, pp. 58-60, vol. 9 (5 pages).

(Continued)

*Primary Examiner* — Robert A Lynch

(57) ABSTRACT

Provided herein are vitrectomy instruments and related systems and methods in which example vitrectomy instruments have multiple rotating cutting edges for severing vitreous fibers. An example vitrectomy instrument may include a handle; an outer tube; and an inner tube configured to be rotated within the outer tube in multiple oscillating rotational cycles. The outer tube may include a port disposed at a distal end thereof. The inner tube may include at least first and second forward cutting edges, so that rotation in a first rotational direction results in both the first and second forward cutting edges cutting vitreous fibers drawn into the port. The inner tube may also include one or more backward cutting edges, so that rotation in a second rotational direction results in one or more backward cutting edges cutting vitreous fibers drawn into the port. Additional forward and/or backward cutting edges may be provided.

15 Claims, 3 Drawing Sheets

(56) References Cited

U.S. PATENT DOCUMENTS

| | | | |
|---|---|---|---|
| 6,527,736 B1 | 3/2003 | Attinger | |
| 8,038,692 B2 | 10/2011 | Valencia | |
| 8,579,929 B2 | 11/2013 | Mackool | |
| 8,845,666 B2 | 9/2014 | Underwood | |
| 9,585,788 B2 | 3/2017 | Underwood | |
| 9,615,969 B2 | 4/2017 | Nissan | |
| 9,693,898 B2 | 7/2017 | Farley | |
| 10,307,290 B2 | 6/2019 | Kern | |
| 10,555,834 B2 | 2/2020 | Charles | |
| 2007/0185514 A1 | 8/2007 | Kirchhevel | |
| 2008/0154292 A1 | 6/2008 | Huculak | |
| 2008/0172077 A1 | 7/2008 | Valencia | |
| 2011/0208207 A1* | 8/2011 | Bowe | A61B 17/50 606/129 |
| 2014/0171997 A1 | 6/2014 | Nissan | |
| 2014/0364886 A1 | 12/2014 | Underwood | |
| 2015/0173948 A1 | 6/2015 | Heeren | |
| 2017/0071788 A1 | 3/2017 | Anderson | |
| 2017/0333252 A1 | 11/2017 | Biancalana | |
| 2018/0008463 A1* | 1/2018 | Charles | A61F 9/00763 |
| 2018/0271705 A1 | 9/2018 | Valencia | |
| 2018/0360660 A1 | 12/2018 | Lopez | |
| 2019/0008680 A1 | 1/2019 | Jochinsen | |
| 2019/0298571 A1 | 10/2019 | Mcdonell | |
| 2020/0016001 A1 | 1/2020 | Mcdonell | |

OTHER PUBLICATIONS

Dugel, P. U., MD. Early Clinical Experience With the Constellation Vision System. Retinal Physician, Special Edition, Feb. 1, 2009 (9 pages).

* cited by examiner

VITRECTOMY INSTRUMENT WITH MULTIPLE ROTATING CUTTING EDGES

PRIORITY CLAIM

This application claims the benefit of priority of U.S. Provisional Patent Application Ser. No. 62/656,230 titled "VITRECTOMY INSTRUMENT WITH MULTIPLE ROTATING CUTTING EDGES," filed on Apr. 11, 2018, whose inventor is Omeed Paydar, which is hereby incorporated by reference in its entirety as though fully and completely set forth herein.

TECHNICAL FIELD

The present disclosure is directed to systems, instruments, and methods for use in medical procedures, and, more particularly, to systems, instruments, and methods for vitrectomy and related procedures.

BACKGROUND

Vitreo-retinal procedures are commonly performed within the posterior segment of the human eye to treat many serious conditions of the posterior segment of the eye. In particular, vitreo-retinal procedures may treat conditions such as age-related macular degeneration (AMD), diabetic retinopathy and diabetic vitreous hemorrhage, macular hole, retinal detachment, epiretinal membrane, cytomegalovirus (CMV) retinitis, and many other ophthalmic conditions.

Such procedures frequently require the cutting and removal of portions of the vitreous humor from the posterior segment of the eye. The vitreous humor is comprised of microscopic fibers or strands within the posterior segment. A surgeon performs vitreo-retinal procedures with a microscope and special lenses designed to provide a clear image of the posterior segment. Several tiny incisions just a millimeter or so in diameter are typically made on the sclera at the pars plana. In a vitrectomy procedure, the surgeon inserts microsurgical instruments through the incisions, including a vitrectomy probe or tip to cut and remove the strands of the vitreous body.

Examples of vitrectomy instruments are disclosed, for example, in U.S. Pat. Nos. 5,176,628, 8,038,692, U.S. Patent Application No. 2008/0172077, U.S. Patent Application No. 2014/0171997, U.S. Patent Application No. 2014/0364886, and U.S. Patent Application No. 2015/0173948. Mechanisms for driving rotation of an inner tube of a vitrectomy instrument and other common features and functions of vitrectomy instruments are known, for example from U.S. Pat. No. 5,176,628 and the INNOVIT® vitrectomy instrument, and therefore the details of such mechanisms are not repeated herein.

In certain prior vitrectomy instruments, the instrument includes an external tube with a port or hole in the tube, for example in the side of the tube. The instrument further includes an internal cutting tube that rotates within the external tube, the internal cutting tube having a cutting edge. Suction is applied to draw the vitreous fibers into the port of the external tube, while the internal cutting tube rotates back and forth at high speed. The internal cutting tube rotates back and forth in an arc less than a full circle (i.e., less than 360 degrees) between a first position and a second position. In rotation from the first position to the second position, the cutting edge of the internal cutting tube approaches and passes by the port, and the action of the cutting edge of the internal cutting tube against the vitreous fibers cuts or breaks the fibers such that they can be suctioned away and removed. The rotation from the second position back to the first position brings the cutting edge back to the first position, ready for another cycle. Thus, in each cycle (from the first position, to the second position, and back to the first position), the cutting edge makes only one cutting action against the fibers.

The removal of vitreous fibers is a sensitive procedure that should be performed efficiently and without damage to the retina or other parts of the eye.

SUMMARY

The present disclosure provides for improvements in vitrectomy instruments and associated systems and methods.

An example of a vitrectomy instrument disclosed herein includes a handle; an outer tube and an inner tube located within the outer tube. The outer tube may include a proximal end, a distal end, and a port formed in the outer tube at the distal end. The outer tube may be connected to the handle at the proximal end of the outer tube. The inner tube may be configured to be rotated within the outer tube in both a first rotational direction from a first position to a second position and a second rotational direction from the second position to the first position. The second rotational direction may be opposite to the first rotational direction. The inner tube may include a distal end and a cutting portion disposed at the distal end of the inner tube. The cutting portion may include at least a first forward cutting edge and a second forward cutting edge that face in the first rotational direction. The first cutting edge and the second cutting edge, in conjunction with the port, may be configured to perform a cutting action to cut material extending through the port when the inner tube is rotated in the first rotational direction from the first position to the second position.

The cutting area of the inner tube may include at least a first opening and a second opening. The forward cutting edges may be located on forward-facing sides of the first and second openings.

The cutting area of the inner tube may include at least a third forward cutting edge that faces in the first rotational direction. The third forward cutting edge, in conjunction with the port, may be configured to perform a cutting action to cut material extending through the port when the inner tube is rotated.

The cutting portion of the inner tube may include at least a first opening, a second opening, and a third opening. The forward cutting edges may be located on forward-facing sides of the first, second, and third openings. Additional openings and/or forward cutting edges in the cutting portion of the inner tube may be provided.

The cutting area of the inner tube may include at least a first backward cutting edge and a second backward cutting edge that face in the second rotational direction. The first backward cutting edge and the second backward cutting edge, in conjunction with the port, may be configured to perform a cutting action to cut material extending through the port when the inner tube is rotated in the second rotational direction.

The cutting portion of the inner tube may include at least a first opening and a second opening. The forward cutting edges may be located on forward-facing sides of the first and second openings, and the backward cutting edges may be located on backward-facing sides of the first and second openings.

The cutting portion of the inner tube may include at least a third backward cutting edge that faces in the second rotational direction. The third backward cutting edge, in conjunction with the port, may be configured to perform a cutting action to cut material extending through the port when the inner tube is rotated in the second rotational direction.

The cutting portion of the inner tube may include at least a first opening, a second opening, and a third opening. The forward cutting edges may be located on forward-facing sides of the first, second, and third openings, and the backward cutting edges may be located on backward-facing sides of the first, second, and third openings. Additional openings and/or backward cutting edges in the cutting portion of the inner tube may be provided.

An example of a system as disclosed herein for performing ophthalmic surgical procedures may include a vitrectomy instrument, a surgical console, and at least one connection line configured for connecting the vitrectomy instrument to the surgical console. The vitrectomy instrument may include a handle, an outer tube, and a distal port formed in the outer tube at the distal end. The outer tube may be connected to the handle at the proximal end of the outer tube. The vitrectomy instrument may also include an inner tube located inside of the outer tube. The inner tube may be configured to be rotated within the outer tube both in a first rotational direction from a first position to a second position and in a second rotational direction from the second position to the first position. The second rotational direction may be opposite the first rotational direction. Movement of the inner tube in the first rotational direction from the first position to the second position and in the second rotational direction from the second position to the first position may define an oscillating rotational cycle. Each oscillating rotational cycle may result in at least two cutting edges of the inner tube crossing the port to perform cutting actions.

The system may rotate the inner tube within the outer tube in multiple oscillating rotational cycles. The rotation of the inner tube may be driven in any manner, such as pneumatically and/or electrically. The at least one connection line may include an aspiration tube configured to aspirate cut vitreous fibers from the vitrectomy instrument to the surgical console.

An example of a method as disclosed herein for performing an ophthalmic surgical procedure may comprise using a vitrectomy instrument as disclosed herein to cut vitreous fibers. The method may include inserting the outer tube of the vitrectomy instrument into an eye with the port adjacent vitreous fibers; applying suction through the vitrectomy instrument in order to draw vitreous fibers into the port; and rotating the inner tube within the outer tube so that rotation in the first rotational direction from the first position to the second position results in both the first forward cutting edge and the second forward cutting edge cutting vitreous fibers drawn into the port.

The vitrectomy instrument may include a third forward cutting edge, and the step of rotating the inner tube within the outer tube in the first rotational direction from the first position to the second position may result in the third forward cutting edge cutting vitreous fibers drawn into the port. Additional forward cutting edges may be provided.

The cutting portion of the inner tube may include at least a first backward cutting edge and a second backward cutting edge that face in the second rotational direction, and the method further may further include rotating the inner tube within the outer tube in the second rotational direction from the second position to the first position, resulting in both the first backward cutting edge and the second backward cutting edge cutting vitreous fibers drawn into the port.

The vitrectomy instrument may include a third backward cutting edge, and the step of rotating the inner tube within the outer tube in the second rotational direction from the second position to the first position may result in the third backward cutting edge cutting vitreous fibers drawn into the port. Additional backward cutting edges may be provided.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the accompanying drawings and the following detailed description.

BRIEF DESCRIPTION OF THE DRAWINGS

The accompanying drawings illustrate implementations of the devices and methods disclosed herein and, together with the description, serve to explain the principles of the present disclosure.

Figure 1:
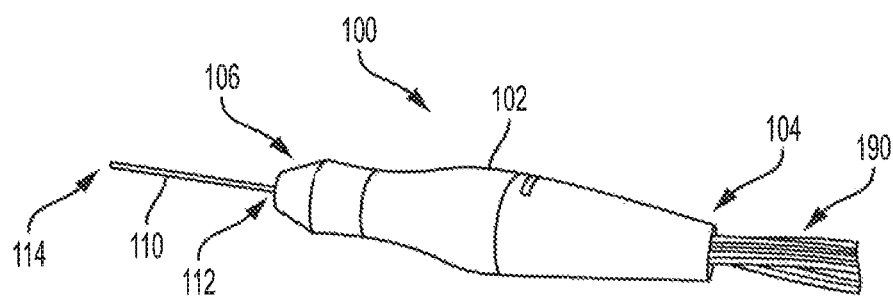
FIG. 1 is a perspective view of an example vitrectomy instrument of the present disclosure.

The accompanying drawings may be better understood by reference to the following detailed description.

DETAILED DESCRIPTION

For the purposes of promoting an understanding of the principles of the present disclosure, reference will now be made to the implementations illustrated in the drawings, and specific language will be used to describe the same. It nevertheless will be understood that no limitation of the scope of the disclosure is intended. Any alterations and further modifications to the described devices, instruments, or methods, and any further application of the principles of the present disclosure, are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure. For simplicity, in some instances the same reference numbers are used throughout the drawings to refer to the same or like parts.

FIG. 1 is an example of a vitrectomy instrument 100 within the present disclosure. The vitrectomy instrument 100 includes a handle 102 that may be used by an operator, such as a physician or other medical professional, to grasp the instrument 100 during, for example, the course of an ophthalmic surgical operation, such as to remove vitreous fibers. The handle 102 has a proximal end 104 and a distal end 106. A needle or outer tube 110 projects from the distal end 106 of the handle 102.

Figure 2:
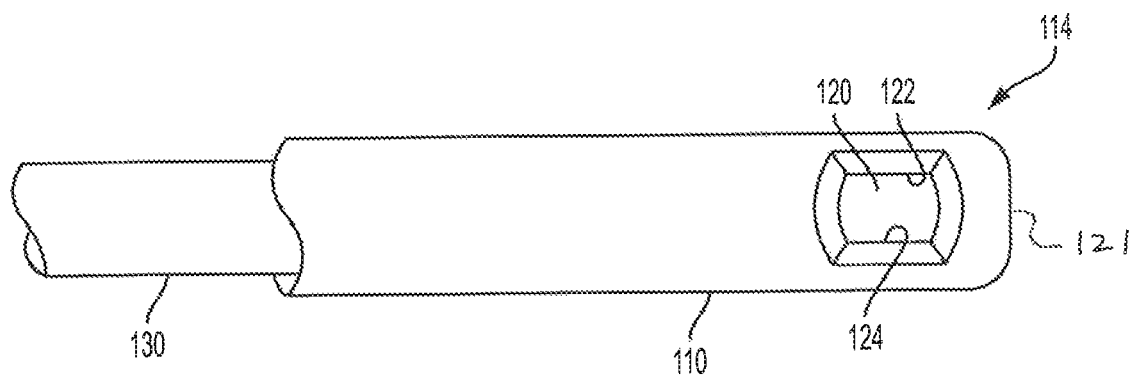
FIG. 2 is a side view of the distal ends of an outer tube and inner tube of the vitrectomy instrument of FIG. 1.

FIG. 2 is a side view of the distal ends of the outer tube 110 and an inner tube 130 of the vitrectomy instrument 100 of FIG. 1. As can be seen in FIG. 1, the outer tube 110 has a proximal end 112 and a distal end 114. The outer tube 110 is connected to the handle 102 at the proximal end 112 of the outer tube 110. As can be seen in FIG. 2, the outer tube 110 comprises an opening or port 120 at its distal end 114. The port 120 extends through the sidewall of the outer tube 110. A terminal end 121 of the outer tube 110 is closed, such that port 120 is the only opening at the distal end 114 of the outer tube 110. In certain variations, more than one port 120 may extend through the sidewall of the outer tube 110 at the distal end 114 thereof.

The inner tube 130 is disposed inside of the outer tube 110 and is configured to be rotated within the outer tube 110 in multiple oscillating rotational cycles. As described in more detail below, each oscillating rotational cycle comprises a forward rotation in a first rotational direction from a first position to a second position and a backward rotation in a second rotational direction from the second position to the first position, wherein the second rotational direction is opposite to the first rotational direction.

As shown in FIG. 1, one or more connection lines 190 extend from or are connected to the proximal end 104 of the handle 102. The connection lines 190 may be used to connect the vitrectomy instrument 100 to a surgical console (not shown) that may be operable to control various aspects of the vitrectomy instrument 100. The connection lines 190 may include one or more electrical connections, pneumatic tubes, aspiration tubes, irrigation tubes, and/or other lines. For example, one or more pneumatic connection lines may be provided for pneumatically driving rotation of the inner tube 130. As another example, one or more electrical connection lines may be provided for electrically driving rotation of the inner tube 130. One or more of the connection lines may comprise an aspiration tube for aspirating materials, such as cut vitreous fibers, from the vitrectomy instrument 100 to the surgical console. For example, an aspiration line may connect suction from the surgical console through the handle 102 and inner tube 130 to the port 120. A reduced pressure or vacuum source in the surgical console draws or aspirates the aspirated material from the eye through the port 120, the inner tube 130, a channel formed in the handle 102, and the aspiration line. The aspirated material may be collected in a collection device. The aspiration may be aided by a saline flushing solution or irrigant that is injected into the surgical site through an irrigation line.

The surgical console may be similar, for example, to that depicted in U.S. Pat. No. 8,579,929, the disclosure of which is incorporated herein by reference in its entirety. The surgical console may be, for example, the CONSTELLATION® Vision System or the INFINITI® Vision System available from Alcon Laboratories, Inc. of Fort Worth, Tex., or a system with similar capabilities in relation to a vitrectomy instrument as disclosed herein. The operation of the vitrectomy instrument 100 may be controlled by the operator using the surgical console using one or more controls. The operation of the vitrectomy instrument 100 may be controlled by the operator using, for example, a foot pedal or other control device.

Figure 3:
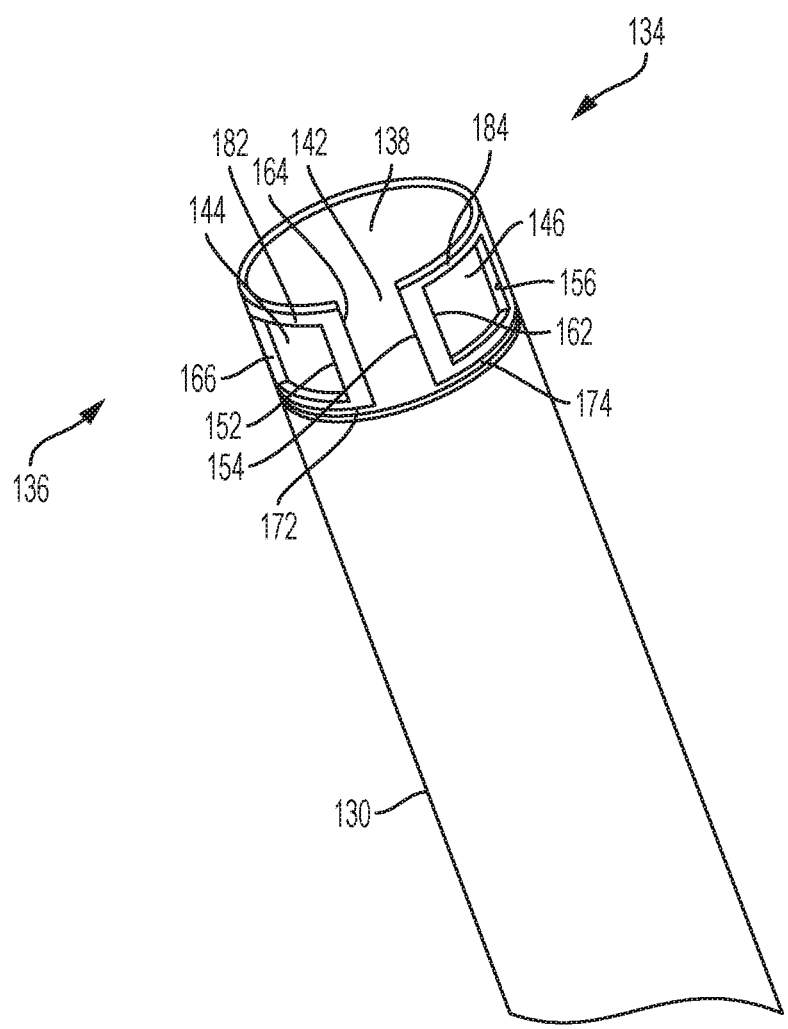
FIG. 3 is a perspective view of the distal end of the inner tube of the vitrectomy instrument of FIG. 1.

FIG. 3 is a perspective view of the distal end 134 of the inner tube 130 of the vitrectomy instrument 100 of FIG. 1. The distal end 134 of the inner tube 130 comprises a cutting portion 136. When the inner tube 130 is assembled within the outer tube 110, the cutting portion 136 is adjacent the port 120 of the outer tube 110. The cutting portion 136 is sized and shaped in order to facilitate cutting interaction between cutting edges of the cutting portion 136 and cutting edges of the port 120 of the outer tube 110 (as described further below).

In the example shown in FIG. 3, when viewed in a circumferential direction around the inner tube 130, the cutting portion 136 comprises openings 142, 144, 146 in the wall of the inner tube 130. In this particular example, opening 142 is a gap that extends distally to the end of the inner tube 130, and openings 144 and 146 are windows that are bounded on all sides. Alternative constructions are possible in which one or more of the openings 144, 146 or other openings are not bounded on all sides.

In the example of FIG. 3, the cutting portion 136 may be viewed as having two blades 182, 184, with each blade 182, 184 being separated on its proximal side from the remainder of the inner tube 130 by a gap 172, 174, respectively. The blades 182, 184 may be biased outwardly in order to help facilitate cutting interaction between the cutting edges of the inner tube 130 (described in more detail below) and the cutting edges of the port 120 of the outer tube 110 (also described in more detail below). Alternatives are possible in which the cutting interaction is facilitated by the size and shape of the cutting portion 136 with or without biasing of the blades 182, 184.

In the example shown in FIG. 3, the cutting portion 136 includes several cutting edges, such as the cutting edges 152, 154, 156, 162, 164 and 166. In this example, the cutting portion 136 includes first forward cutting edge 152, second forward cutting edge 154, and third forward cutting edge 156, each of which is disposed in a configuration to perform a cut in a first rotational direction. The cutting portion 136 also includes first backward cutting edge 162, second backward cutting edge 164, and third backward cutting edge 166, each of which is disposed in a configuration to perform a cut in a second rotational direction that is opposite the first rotational direction. For example, if the first rotational direction or forward direction is clockwise, then the second rotational direction or backward direction is counterclockwise. Alternatively, if the first rotational direction or forward direction is counterclockwise, then the second rotational direction or backward direction is clockwise.

The number of openings and/or cutting edges of the cutting portion 136 of the inner tube 130 may be varied. For example, the cutting portion 136 of the inner tube 130 may have three openings 142, 144, 146 with three cutting edges operable to cut when the inner tube 130 is rotated in each rotational direction. Thus, in the example shown, six cutting edges 152, 154, 156, 162, 164, and 166 are provided, as shown in FIG. 3. Alternatively, the same number of openings may be used, but fewer than all of the edges may be cutting edges, resulting in fewer than six cutting edges. In some implementations, the cutting portion 136 having three openings may have a minimum of two cutting edges for cutting when the inner tube 130 is rotated in each of the rotational directions. In other examples, there may be two or more openings, and two or more cutting edges facing in the same direction. For example, an embodiment may have two, three, four, or more openings, with two, three, four, or more cutting edges facing in the forward direction, with the option of also having one or more cutting edges facing in the backward direction.

As can be seen in FIG. 3, one set of cutting edges 152, 154, and 156 face in one direction, while the other set of cutting edges 162, 164, and 166 face in the opposite direction. That is, the cutting edges 152, 154, and 156 are adapted to cut when the inner tube 130 is rotated in a first rotational direction, and the cutting edges 162, 164, and 166 are adapted to cut when the inner tube 130 is rotated in a second rotational direction. Thus, for example, if the direction in which the cutting edges 152, 154, and 156 face is considered the forward direction, then the direction in which the cutting edges 162, 164, and 166 face is considered the backward direction. Considering this orientation, the forward cutting edges 152, 154, and 156 are located on forward-facing sides of the openings 144, 142, 146, respectively, and the backward cutting edges 162, 164, and 166 are located on backward-facing sides of the openings 146, 142, 144, respectively.

As mentioned above, the inner tube 130 is configured to be rotated within the outer tube 110 in multiple oscillating rotational cycles. Each oscillating rotational cycle comprises a forward rotation in a first rotational direction from a first position to a second position and a backward rotation in a second rotational direction from the second position to the first position, where the second rotational direction is opposite to the first rotational direction. When the vitrectomy instrument 100 is used to remove vitreous fibers, the inner tube 130 is configured so that the forward rotation in the first rotational direction from the first position to the second position results in both the first forward cutting edge and the second forward cutting edge (and optionally a third or more forward cutting edges) cutting vitreous fibers drawn into the port 120 of the outer tube 110. In addition, when one or more backward cutting edges are employed, backward rotation in the second rotational direction from the second position to the first position results in any backward cutting edges cutting vitreous fibers drawn into the port 120 of the outer tube 110.

An example method of performing an ophthalmic surgical procedure in accordance with the disclosure includes using a vitrectomy instrument as disclosed herein, having a handle, an outer tube with a port at its distal end, and an inner tube located inside of the outer tube and configured to be rotated within the outer tube in multiple oscillating rotational cycles. In use, the operator inserts the outer tube into a patient's eye with the port adjacent vitreous fibers. Suction may be applied through the inner tube of the vitrectomy instrument via an aspiration line, and the inner tube within the outer tube may be rotated in an oscillating motion. The operator may cause application of suction and rotation of the inner tube by manipulation of one or more controls provided, for example, on the instrument, console, or located elsewhere.

Each oscillating rotational cycle of the inner tube may include a forward rotation in a first rotational direction from a first position to a second position and a backward rotation in a second rotational direction from the second position to the first position, where the second rotational direction is opposite to the first rotational direction. The inner tube includes a distal end having a cutting portion. The cutting portion may include at least a first forward cutting edge and a second forward cutting edge that face in the first rotational direction. In each rotational cycle, when the inner tube is rotated within the outer tube in the first rotational direction from the first position to the second position, both the first forward cutting edge and the second forward cutting edge cut vitreous fibers drawn into the port, thereby resulting in multiple cuts per cycle. In accordance with variations as described above, the instrument may have two, three, four or more cutting edges facing in one direction, and optionally one, two, three, four or more cutting edges facing in the opposite direction, resulting in two or more cuts per cycle in the forward direction, and optionally one or more additional cuts per cycle in the backward direction.

Figure 4A:
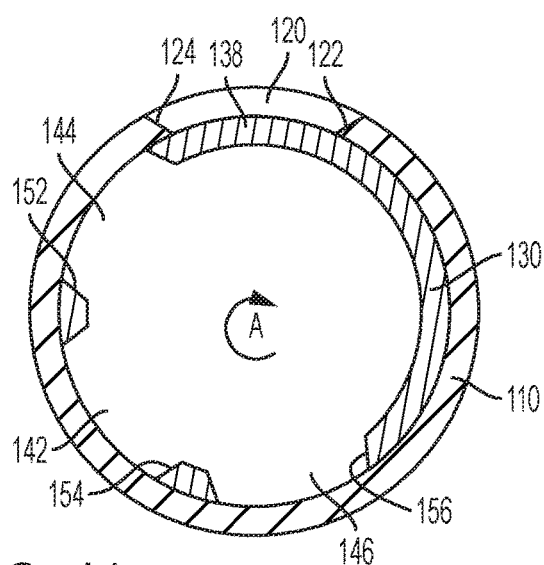
FIGS. 4A-4E show cross-sectional views of the distal ends of the outer tube and inner tube of the vitrectomy instrument of FIG. 1, showing stages in oscillating rotational movement of the inner tube within the outer tube.

FIGS. 4A-4E show cross-sectional views of the distal ends of the outer tube 110 and the inner tube 130 of the vitrectomy instrument 100, showing stages in a single cycle of an example of an oscillating rotational movement of the inner tube 130 within the outer tube 110. The cross-section of FIGS. 4A-4E extend through the port 120 of the outer tube 110 and the cutting portion 136 of the inner tube 130. FIG. 4A illustrates a first position of the inner tube 130 within the outer tube 110. In this first position, the port 120 of the outer tube 110 is blocked by a solid portion 138 of the cutting portion 136 of the inner tube 130. The suction that is applied through the inner tube 130 via the aspiration line is blocked by this solid portion 138 covering the port 120.

The first rotational direction or forward direction is labeled by the arrow A. As the inner tube 130 rotates in the forward direction, the opening 144 crosses the port 120, whereby the suction acts on the vitreous fibers and draws vitreous fibers through the port 120 and opening 144. As the inner tube 130 continues to rotate in the forward direction, the first forward cutting edge 152 moves toward the cutting edge 122 of the outer tube 110 with the vitreous fibers therebetween, and the action of the first forward cutting edge 152 in conjunction with the cutting edge 122 cuts, severs, or breaks the vitreous fibers. The portions of the vitreous fibers that are cut off are suctioned away through the vitrectomy instrument 100 and aspiration line.

Figure 4B:
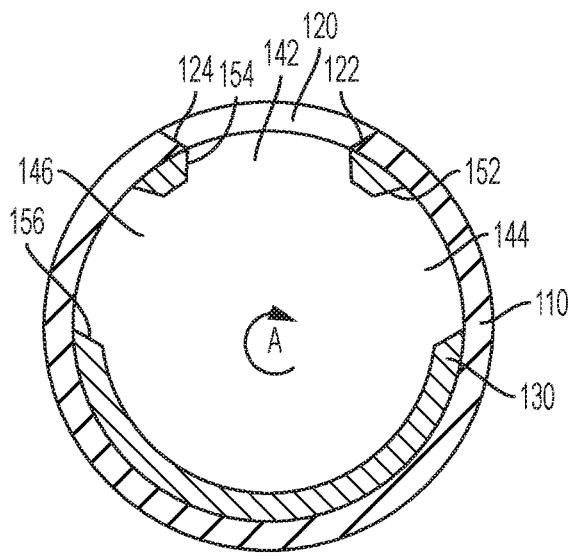

FIG. 4B shows a snapshot of the rotation just after the first forward cutting edge 152 has moved past the cutting edge 122. At this stage the opening 142 is crossing the port 120, as shown in FIG. 4B, whereby the suction acts on the vitreous fibers and draws vitreous fibers through the port 120 and opening 142. As the inner tube 130 continues to rotate in the forward direction, the second forward cutting edge 154 moves toward the cutting edge 122 of the outer tube 110 with the vitreous fibers therebetween, and the action of the second forward cutting edge 154 in conjunction with the cutting edge 122 cuts, severs, or breaks the vitreous fibers. The portions of the vitreous fibers that are cut off are suctioned away through the vitrectomy instrument 100 and aspiration line.

As the inner tube 130 continues to rotate in the forward direction, the opening 146 crosses the port 120, whereby the suction acts on the vitreous fibers and draws vitreous fibers through the port 120 and opening 146. As the inner tube 130 continues to rotate in the forward direction, the third forward cutting edge 156 moves toward the cutting edge 122 of the outer tube 110 with the vitreous fibers therebetween, and the action of the third forward cutting edge 156 in conjunction with the cutting edge 122 cuts, severs, or breaks the vitreous fibers. The portions of the vitreous fibers that are cut off are suctioned away through the vitrectomy instrument 100 and aspiration line.

Figure 4C:
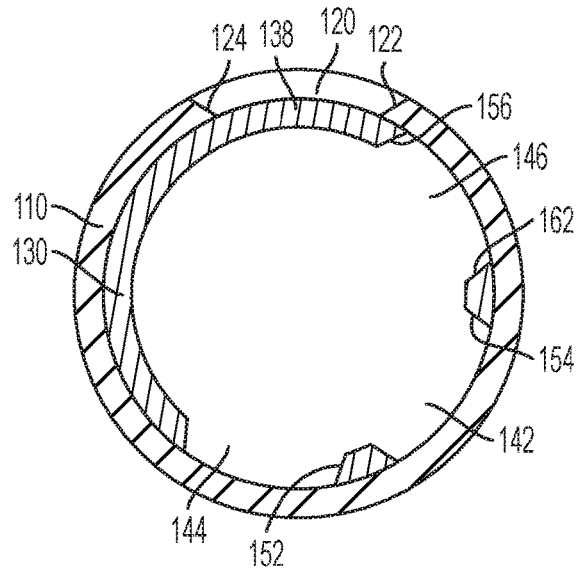

FIG. 4C shows a snapshot just after the third forward cutting edge 156 has moved past the cutting edge 122. At this stage, the port 120 of the outer tube 110 is blocked by solid portion 138 of the cutting portion 136 of the inner tube 130. FIG. 4C represents the second position, which is the position at which rotation in the forward direction is stopped and rotation in the second rotational direction or backward direction, represented by arrow B, begins.

As the inner tube 130 rotates from the second position in the backward direction, the opening 146 again crosses the port 120, whereby the suction acts on the vitreous fibers and draws vitreous fibers through the port 120 and opening 146. As the inner tube 130 continues to rotate in the backward direction, the first backward cutting edge 162 moves toward the cutting edge 124 of the outer tube 110 with the vitreous fibers therebetween, and the action of the first backward cutting edge 162 in conjunction with the cutting edge 124 cuts, severs, or breaks the vitreous fibers. The portions of the vitreous fibers that are cut off are suctioned away through the vitrectomy instrument 100 and aspiration line.

Figure 4D:
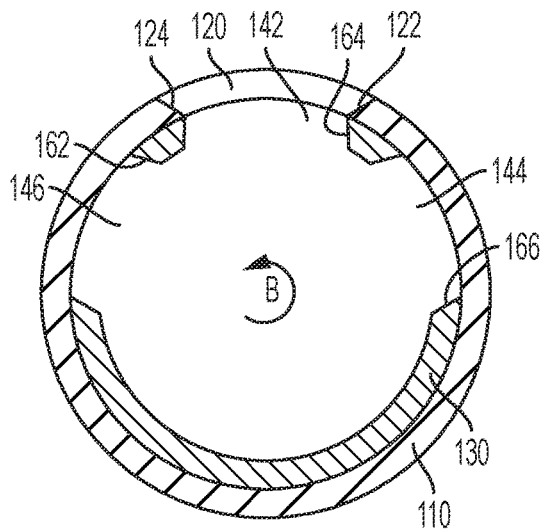

FIG. 4D shows a snapshot of the rotation just after the first backward cutting edge 162 has moved past the cutting edge 124. This snapshot is similar to that of FIG. 4B except that the inner tube 130 is moving in the opposite direction. At this stage the opening 142 is crossing the port 120, as shown in FIG. 4D, whereby the suction acts on the vitreous fibers and draws vitreous fibers through the port 120 and opening 142. As the inner tube 130 continues to rotate in the backward direction, the second backward cutting edge 164 moves toward the cutting edge 124 of the outer tube 110 with the vitreous fibers therebetween, and the action of the second backward cutting edge 164 in conjunction with the cutting edge 124 cuts, severs, or breaks the vitreous fibers. The portions of the vitreous fibers that are cut off are suctioned away through the vitrectomy instrument 100 and aspiration line.

As the inner tube 130 continues to rotate in the backward direction, the opening 144 crosses the port 120, whereby the suction acts on the vitreous fibers and draws vitreous fibers through the port 120 and opening 144. As the inner tube 130 continues to rotate in the backward direction, the third backward cutting edge 166 moves toward the cutting edge 124 of the outer tube 110 with the vitreous fibers therebetween, and the action of the third backward cutting edge 166 in conjunction with the cutting edge 124 cuts, severs, or breaks the vitreous fibers. The portions of the vitreous fibers that are cut off are suctioned away through the vitrectomy instrument 100 and aspiration line.

Figure 4E:
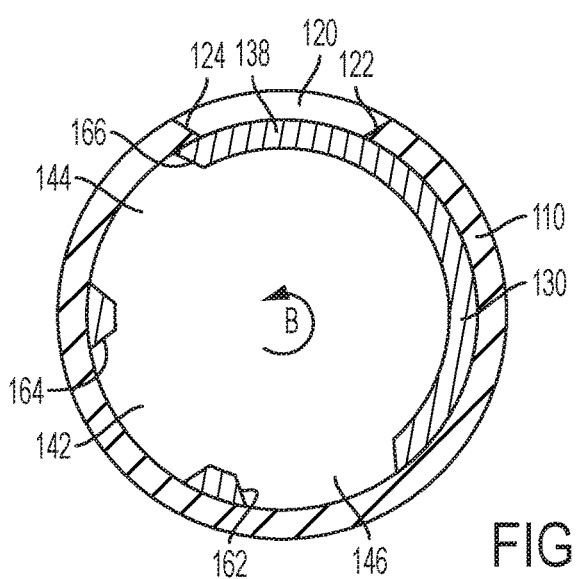

FIG. 4E shows a snapshot just after the third backward cutting edge 166 has moved past the cutting edge 124. At this stage, the port 120 of the outer tube 110 is blocked by solid portion 138 of the cutting portion 136 of the inner tube 130. FIG. 4E shows a similar condition as FIG. 4A. Like FIG. 4A, FIG. 4E represents the first position, which is the position at which rotation in the second rotational direction or backward direction, represented by arrow B, is stopped, and rotation in the first rotational direction or forward direction, represented by arrow A, begins again, to start a new cycle.

As can be seen from FIGS. 4A-4E and the above description, in each cycle of the inner tube 130, the vitrectomy instrument 100 makes three cuts of vitrectomy fibers in the first direction and three cuts of vitrectomy fibers in the second direction, for six cuts per cycle. In alternate embodiments as described above, a vitrectomy instrument as described may make two, three, four, or more cuts of vitrectomy fibers in the first direction, and optionally an additional one, two, three, four, or more cuts of vitrectomy fibers in the second direction, for two or more cuts per cycle.

The arc of rotation in each direction of an inner tube in accordance with embodiments described herein may be less than a full circle, i.e., less than 360 degrees. In the example shown in FIGS. 4A-4E, the arc of rotation in each direction is more than 180 degrees. For example, the arc of rotation may be within a range of 180 degrees to 200 degrees. In other examples, the arc of rotation may be 180 degrees, or less than 180 degrees.

In an alternative method of use of the vitrectomy instrument 100 from that illustrated in FIGS. 4A-4E, the first position may be the position at which the opening 144 is aligned with the port 120, and the second position may be the position at which the opening 146 is aligned with the port 120. Rotating the inner tube 130 in the forward direction from the first position to the second position results in the cutting edges 152 and 154 cutting fibers in the forward direction. Rotating the inner tube 130 in the backward direction from the second position to the first position results in the cutting edges 162 and 164 cutting fibers in the backward direction. This variation, which results in four cuts per cycle, has the advantage of not blocking the port 120 with the solid portion 138.

In an example operation, the inner tube 130 may be driven (for example pneumatically) at 5,000 cycles per minute. In an example with two cuts per cycle, a vitrectomy instrument as described herein can make 10,000 cuts per minute. In an example with four cuts per cycle, a vitrectomy instrument as described herein can make 20,000 cuts per minute. In an example with six cuts per cycle, a vitrectomy instrument as described herein can make 30,000 cuts per minute.

A vitrectomy instrument as described herein has significant advantages over the prior art. For example, in the prior INNOVIT® vitrectomy instrument and in U.S. Pat. No. 5,176,628, the rotational cutter makes only one cut per cycle. As shown in U.S. Pat. No. 5,176,628, one cycle consists of moving from the position shown in FIG. 11 of that patent to the position shown in FIG. 12 of that patent and then back to the position shown in FIG. 11 of that patent, resulting in only one cut per cycle. By contrast, embodiments as described herein provide efficiencies in an increased number of cuts per cycle, significantly improving operation, among other advantages, including longer duty cycle, less interruption in aspiration, safety advantages, and improved patient outcome. In addition, with respect to certain variations described above, blockage of the port of the outer tube may be minimized or avoided, providing further advantages over the prior art. The rotational cutter also avoids disadvantages associated with longitudinally reciprocating cutters, such as the disadvantageous pumping action that can be experienced with such a cutter.

A vitrectomy instrument in accordance with implementations of the disclosure may be made of any suitable material. The outer tube and inner tube may be, for example, a metallic material, such as stainless steel or a titanium alloy. The dimensions may be any suitable dimensions for use in a vitrectomy procedure. For example, the outer tube may have an outer diameter sized for a 23 gauge, 25 gauge, or 27 gauge procedure.

Persons of ordinary skill in the art will recognize that, in addition to cutting and aspiration of vitreous fibers, instruments as described herein may also be used for other procedures, such as membrane cutting and aspiration, dissecting tissue, and/or lens removal.

Persons of ordinary skill in the art will appreciate that the implementations encompassed by the present disclosure are not limited to the particular exemplary implementations described above. In that regard, although illustrative implementations have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A vitrectomy instrument comprising:
   a handle;
   an outer tube comprising:
      a proximal end;
      a distal end; and
      at least two ports formed in the outer tube at the distal end, the outer tube connected to the handle at the proximal end of the outer tube; and an inner tube located inside of the outer tube and configured to be rotated within the outer tube in both a first rotational direction from a first position to a second position and a second rotational direction from the second position to the first position, the second rotational direction being opposite to the first rotational direction, the inner tube comprising:
a distal end;
a cutting portion disposed at the distal end of the inner tube, the cutting portion comprising at least a first forward cutting edge and a second forward cutting edge that face in the first rotational direction such that the first forward cutting edge and the second forward cutting edge, in conjunction with a port of the at least two ports, are configured to perform a cutting action to cut material extending through the port of the at least two ports when the inner tube is rotated in the first rotational direction from the first position to the second position;
wherein the cutting portion of the inner tube further comprises at least a third forward cutting edge that faces in the first rotational direction, wherein the third forward cutting edge, in conjunction with a port of the at least two ports, is configured to perform a cutting action to cut material extending through the port of the at least two ports when the inner tube is rotated in the first rotational direction from the first position to the second position;
wherein the cutting portion of the inner tube further comprises at least a first opening, a second opening, and a third opening, wherein the third opening comprises a gap, between the first opening and the second opening, extending to the distal end of the inner tube, and wherein the first and second openings are windows in the inner tube that are bounded on all sides by the inner tube;
wherein the forward cutting edges are located on forward-facing sides of the openings.

2. The vitrectomy instrument according to claim 1, wherein the cutting portion of the inner tube further comprises at least a first backward cutting edge and a second backward cutting edge that face in the second rotational direction, wherein the first backward cutting edge and the second backward cutting edge, in conjunction with a port of the at least two ports, are configured to perform a cutting action to cut material extending through the port of the at least two ports when the inner tube is rotated in the second rotational direction from the second position to the first position.

3. The vitrectomy instrument according to claim 2, wherein the backward cutting edges are located on backward-facing sides of the openings.

4. The vitrectomy instrument according to claim 2, wherein the cutting portion of the inner tube further comprises at least a third backward cutting edge that faces in the second rotational direction, wherein the third backward cutting edge, in conjunction with a port of the at least two ports, is configured to perform a cutting action to cut material extending through the port of the at least two ports when the inner tube is rotated in the second rotational direction.

5. The vitrectomy instrument according to claim 4, wherein the backward cutting edges are located on backward-facing sides of the openings.

6. A system for performing ophthalmic surgical procedures comprising:
(i) vitrectomy instrument comprising:
a handle;
an outer tube comprising:
a proximal end;
a distal end; and
at least two ports formed in the outer tube at the distal end, the outer tube connected to the handle at the proximal end of the outer tube; and
an inner tube located inside of the outer tube and configured to be rotated within the outer tube both in a first rotational direction from a first position to a second position and a second rotational direction from the second position to the first position, the second rotational direction being opposite to the first rotational direction, the inner tube comprising:
a distal end;
a cutting portion disposed at the distal end of the inner tube, the cutting portion comprising at least a first forward cutting edge and a second forward cutting edge that face in the first rotational direction, such that the first forward cutting edge and the second forward cutting edge, in conjunction with a port of the at least two ports, are configured to perform a cutting action to cut material extending through the port of the at least two ports when the inner tube is rotated in the first rotational direction from the first position to the second position;
wherein the cutting portion of the inner tube further comprises at least a third forward cutting edge that faces in the first rotational direction, wherein the third forward cutting edge, in conjunction with a port of the at least two ports, is configured to perform a cutting action to cut material extending through the port of the at least two ports when the inner tube is rotated in the first rotational direction from the first position to the second position;
wherein the cutting portion of the inner tube further comprises at least a first opening, a second opening, and a third opening, wherein the third opening comprises a gap, between the first opening and the second opening, extending to the distal end of the inner tube, and wherein the first and second openings are windows in the inner tube that are bounded on all sides by the inner tube;
wherein the forward cutting edges are located on forward-facing sides of the openings;
(ii) a surgical console; and
(iii) at least one connection line configured for connecting the vitrectomy instrument to the surgical console.

7. The system for performing ophthalmic surgical procedures according to claim 6, wherein movement of the inner tube in the first rotational direction from the first position to the second position and in the second rotational direction from the second position to the first position comprises an oscillating rotational cycle, and wherein each oscillating rotational cycle results in at least two cutting edges of the inner tube crossing a port of the at least two ports to perform cutting actions.

8. The system for performing ophthalmic surgical procedures according to claim 7, wherein the rotation of the inner tube is driven pneumatically.

9. The system for performing ophthalmic surgical procedures according to claim 7, wherein the rotation of the inner tube is driven electrically.

10. The system for performing ophthalmic surgical procedures according to claim 6, wherein the at least one connection line comprises an aspiration tube configured to aspirate cut vitreous fibers from the vitrectomy instrument to the surgical console.

11. A method of performing an ophthalmic surgical procedure comprising:
(i) using a vitrectomy instrument comprising:
a handle;
an outer tube comprising:
a proximal end;
a distal end; and
at least two ports formed in the outer tube at the distal end, the outer tube connected to the handle at the proximal end of the outer tube; and
an inner tube located inside of the outer tube and configured to be rotated within the outer tube both in a first rotational direction from a first position to a second position and a second rotational direction from the second position to the first position, the second rotational direction being opposite to the first rotational direction, the inner tube comprising:
a distal end; and
a cutting portion disposed at the distal end of the inner tube, the cutting portion comprising at least a first forward cutting edge and a second forward cutting edge that face in the first rotational direction;
wherein the cutting portion of the inner tube further comprises at least a third forward cutting edge that faces in the first rotational direction, wherein the third forward cutting edge, in conjunction with a port of the at least two ports, is configured to perform a cutting action to cut material extending through the port of the at least two ports when the inner tube is rotated in the first rotational direction from the first position to the second position;
wherein the cutting portion of the inner tube further comprises at least a first opening, a second opening, and a third opening, wherein the third opening comprises a gap, between the first opening and the second opening, extending to the distal end of the inner tube, and wherein the first and second openings are windows in the inner tube that are bounded on all sides by the inner tube;
wherein the forward cutting edges are located on forward-facing sides of the openings;
(ii) inserting the outer tube into an eye with the at least two ports adjacent to vitreous fibers;
(iii) applying suction through the vitrectomy instrument in order to draw vitreous fibers into the at least two ports; and
(iv) rotating the inner tube within the outer tube in the first rotational direction from the first position to the second position to cause both the first forward cutting edge and the second forward cutting edge to cut vitreous fibers drawn into a port of the at least two ports.

12. The method according to claim 11, wherein the cutting portion of the inner tube comprises at least a first opening and a second opening.

13. The method according to claim 11, wherein the cutting portion of the inner tube further comprises at least a third forward cutting edge that faces in the first rotational direction, and wherein the step of rotating the inner tube within the outer tube in the first rotational direction from the first position to the second position results in the third forward cutting edge cutting vitreous fibers drawn into a port of the at least two ports.

14. The method according to claim 11, wherein the cutting portion of the inner tube further comprises at least a first backward cutting edge and a second backward cutting edge that face in the second rotational direction, wherein the method further comprises rotating the inner tube within the outer tube in the second rotational direction from the second position to the first position, resulting in both the first backward cutting edge and the second backward cutting edge cutting vitreous fibers drawn into a port of the at least two ports.

15. The method according to claim 14, wherein the cutting portion of the inner tube further comprises at least a third backward cutting edge that faces in the second rotational direction, wherein the step of rotating the inner tube within the outer tube in the second rotational direction from the second position to the first position results in the third backward cutting edge cutting vitreous fibers drawn into a port of the at least two ports.

* * * * *